(12) United States Patent
Haider et al.

(10) Patent No.: US 7,466,849 B2
(45) Date of Patent: Dec. 16, 2008

(54) METHOD AND APPARATUS FOR ACQUISITION AND EVALUATION OF IMAGE DATA OF AN EXAMINATION SUBJECT

(75) Inventors: Sultan Haider, Erlangen (DE); Peter Kreisler, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 56 days.

(21) Appl. No.: 11/473,771

(22) Filed: Jun. 23, 2006

(65) Prior Publication Data

US 2007/0012880 A1 Jan. 18, 2007

(30) Foreign Application Priority Data

Jun. 23, 2005 (DE) .................. 10 2005 029 242

(51) Int. Cl.
*G06K 9/00* (2006.01)
(52) U.S. Cl. ...................... 382/128; 600/407
(58) Field of Classification Search ................. 382/128, 382/130, 132
See application file for complete search history.

(56) References Cited

U.S. PATENT DOCUMENTS

| | | | |
|---|---|---|---|
| 5,261,406 A * | 11/1993 | MacKay et al. ............. 600/431 |
| 5,740,267 A | 4/1998 | Echerer et al. |
| 6,135,960 A | 10/2000 | Holmberg |
| 6,195,409 B1 | 2/2001 | Chang et al. |
| 6,484,048 B1 * | 11/2002 | Hoshino et al. ............ 600/410 |
| 6,529,758 B2 | 3/2003 | Shahidi |
| 6,968,224 B2 * | 11/2005 | Kessman et al. ........... 600/407 |
| 7,212,661 B2 * | 5/2007 | Samara et al. ............. 382/131 |
| 7,231,076 B2 * | 6/2007 | Fu et al. .................. 382/131 |
| 2002/0198447 A1 | 12/2002 | Van Muiswinkel et al. |
| 2003/0144589 A1 | 7/2003 | Roell |
| 2005/0010107 A1 | 1/2005 | Shen |
| 2005/0065424 A1 * | 3/2005 | Shah et al. ............... 600/407 |
| 2005/0065617 A1 | 3/2005 | Moctezuma de la Barrera et al. |

FOREIGN PATENT DOCUMENTS

DE 103 46 410 A1 5/2005
EP 0 429 148 A1 5/1991

* cited by examiner

*Primary Examiner*—Yosef Kassa
*Assistant Examiner*—Katrina Fujita
(74) *Attorney, Agent, or Firm*—Schiff Hardin LLP

(57) ABSTRACT

In a method and apparatus for acquisition and evaluation of image data of an examination subject that are to be created with at least one imaging medical imaging apparatus, generation of a whole-body overview image of the examination subject is generated and selection of an anatomical region in the whole-body overview image is selected. A point in the selected anatomical region is established that forms the origin of a whole-body coordinate system relating to the examination subject, and establishment of an associated, subject-related coordinate system is established/Upon a later examination with a medical imaging apparatus, a whole-body overview image and/or a partial image containing the origin and/or another marker point is/are generated, and examination (diagnostic) images of the examination subject (S3), are generated. Using new whole-body overview images and/or the partial image, the examination images and spatially arranged in the original whole-body coordinate system dependent on a comparison of at least one item of image information of the examination image with at least one item of image information of the whole-body overview image and/or at least one item of information of the partial image that is related to the whole-body coordinate system.

19 Claims, 2 Drawing Sheets

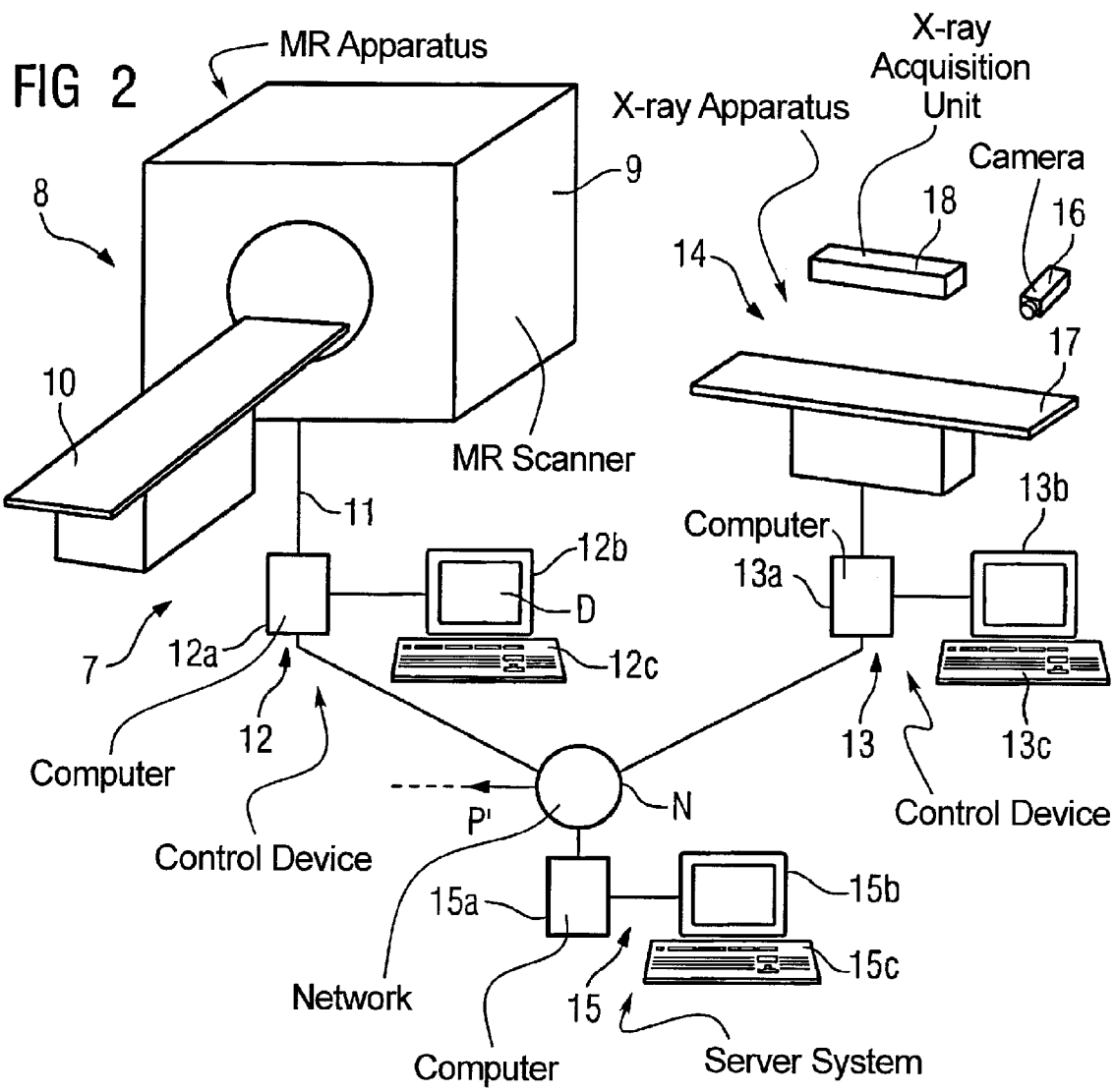
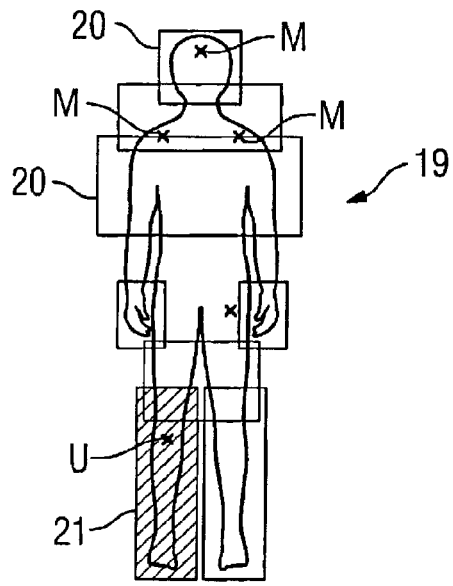

METHOD AND APPARATUS FOR ACQUISITION AND EVALUATION OF IMAGE DATA OF AN EXAMINATION SUBJECT

BACKGROUND OF THE INVENTION

1. Field of the Invention

The present invention concerns a method for acquisition and evaluation of image data of an examination subject that are generated with at least one medical imaging apparatus as well as an associated apparatus.

2. Description of the Prior Art

In the framework of the examination of a patient, exposures are often produced with medical imaging apparatuses in order, for example, to generate a diagnosis or a finding or to be able to plan a therapy. It is thereby frequently not sufficient to produce an exposure or an exposure series once with an examination apparatus. Rather, exposures are often acquired at specific time intervals, for example to monitor a recovery or an etiopathology (course of a disease), possibly also exposures of other body regions insofar as new diseases could occur or interactions are to be monitored.

An examination with different examination apparatuses (for example with a computed tomography apparatus, a magnetic resonance system or a ultrasound apparatus) is additionally frequently necessary for a concluding examination that enables a qualified diagnosis and treatment. The produced image exposures are normally spatially associated with each other using a coordinate system that is predetermined by the examination apparatus. Alternatively, patient-specific coordinate systems that are specific to the respective examination and the directly-observed examination region can be used.

In the use of apparatus-specific coordinate systems, there is the problem of the comparability of exposures that have been produced with different apparatuses. With region-related patient coordinate systems, there is the problem that exposures of other body regions or exposures with different orientations cannot be arranged or compared, or can only be arranged or compared with difficulty. It is extraordinarily difficult to interpret exposures that were produced with different apparatuses or at different times, or of different examination regions, in the evaluation and the subsequent finding.

SUMMARY OF THE INVENTION

An object of the present invention is to provide a method for acquisition and evaluation of image data of an examination subject that are obtained with at least one medical imaging apparatus, which allows a faster and qualitatively better evaluation compared to conventional methods.

This object is achieved in accordance with the invention by a method that includes the steps of:

Generating a whole-body overview image of the examination subject and selection of an anatomical region in the whole-body overview image.

Establishing a point in the selected anatomical region, this point forming the origin of a whole-body coordinate system relating to the examination subject, and establishing an associated, subject-related coordinate system.

In a later examination with a medical examination apparatus, re-creating a whole-body overview image and/or a partial image including the origin and/or another marker point, and generating examination images of the examination subject.

With the aid of the new whole-body overview image and/or the partial image, spatially arranging the examination (diagnostic) images in the original whole-body coordinate system dependent on a comparison of at least one item of image information of the examination image with at least one item of image information of the whole-body overview image and/or at least one item of information of the partial image that is related to the whole-body coordinate system.

According to the invention, a whole-body overview image of an examination subject (for example a person or an animal) is thus produced before the generation of one or more actual diagnostic images. This whole-body overview image is used as an examination guide, and is shown on a display or monitor. This overview image completely reproduces the body of the examination subject, allowing specific anatomical regions (such as the head, the chest, the abdomen or also the arms and legs) to be differentiated.

Such an anatomical region is selected in the whole-body overview image by electronic interaction with the overview image, and a point that represents the origin of a coordinate system regarding the entire body of the examination subject is established within this selected anatomical region. This point forming the origin can be a specific point in the body of the examination subject that is used in examinations such as what is known as an anatomical marker, for example the clavicle protuberance or a specific vertebra or a back prominence and the like. A coordinate system that represents a whole-body coordinate system for the respective examination subject is established with regard to this origin point. An orthogonal trihedron with axial directions is appropriately selected for this coordinate system, the axial directions thereof corresponding to the body-relative axes normally used in anatomy.

Finally, examination images of the examination subject can be created with a medical imaging apparatus, and these examination images can be spatially associated with the whole-body coordinate system using the whole-body overview image, with the position of the anatomical information represented as image information in the examination images being established clearly (namely with regard to the coordinate system defined above). It is likewise possible to implement an examination only later or to implement one or more follow-up examinations in the event that examination images have already been acquired and arranged in the coordinate system as described in the preceding. Such follow-up examinations, if applicable, can be implemented with other medical examination apparatuses. It is thus possible for an x-ray exposure to be made initially with ultrasound exposures being produced in the framework of a subsequent examination.

If a later examination (that can be a follow-up examination) is undertaken, a whole-body overview image and/or a partial image are thus re-created, the partial image showing not the entire body but rather a section thereof that contains the origin point and/or another marker point. Like the first overview image, this overview image or, respectively, partial image serves as a reference image and is accordingly stored. The new whole-body overview image or partial image serves for the determination of the coordinates for the examination images to be acquired now in order to be able to arrange these spatially in the original whole-body coordinate system. For this purpose, a comparison of at least one item of image information of the examination (diagnostic) image with at least one item of image information of the whole-body overview image and and/or at least one item of information of the partial image that relates to the whole-body coordinate system is implemented. An image processor can be used that compares the image data of the different images and detects commonalities, for example also with the aid of defined anatomical regions or markers. The result of the spatial arrangement can ultimately be displayed on an image output unit as a whole-body image and/or partial image with which examination images (which are possibly shown with lower resolution or merely as outlines) placed within this overview image are shown.

The inventive method thus offers the possibility to quickly compare examination images of examinations that have occurred at different points in time or were implemented with different apparatuses using the spatial arrangement in the whole-body coordinate system. Through the knowledge of the associated coordinates of the whole-body coordinate system, it is immediately clear where the respective image is to be arranged in the patient body and how it compares with earlier exposures for evaluation. If a doctor or technician who is occupied with the evaluation of the image data searches for exposures of specific regions, he or she can simply search through a data processing device by specification of the coordinates of the whole-body coordinate system. Like the examination planning, the navigation through the (often large) quantity of image data is significantly simplified; reference to a single coordinate system that can be maintained unchanged for all examinations of the respective patient now suffices. The quality of the coverage thus can be distinctly improved while at the same time the examination planning (for example given the production of real-time exposures) is simplified.

According to the invention, the electronic interaction with the overview image (or the data representing the overview image) for selecting the anatomical region can be selected automatically and/or on the part of the user. An automatic selection can ensue, for example, such that a marked ariatomical region is defined dependent on the apparatus that is used for generation of the whole-body overview image in the context of its predominant usage. This automatic selection, for example, can be predetermined by an operator of an examination apparatus or can be pre-selected by a program. It is likewise possible for the anatomical region to be selected by the user, such as by a region that is pre-selected at a default selection being replaced by another.

Furthermore, in accordance with the invention the user can select the anatomical region freely or from a number of predetermined regions. It is possible for various separated regions (for example separated or boxed off from one another by lines) to be shown to the user in the whole-body overview image, with additional text information (such as, for example, "head" or "thorax") also being possibly presented. Such predetermined regions can also be indicated with different colors. A free selection is alternatively possible, for example such that the user enters selection boxes or intersecting lines via an input device with an associated image processing functionality of a program in order to specify the boundary of the desired region.

Predetermined anatomical regions can be determined in accordance with the invention using geometric data and/or fitting algorithms and/or decision rules. Functionalities hereby also can be determined that are already implemented anyway for the required image evaluation in medical imaging apparatuses. To determine the anatomical regions using geometric data, for example, data are used that determine proportions in the human body or that show and compare typical specifications for intervals between marked anatomical points. Fitting algorithms detect specific curve contours, so that a reference to an anatomical region can be produced based thereon. To establish boundaries, decision rules (such as, for example, practical knowledge (know-how as well) can be employed by a computer using connections that occur frequently or always in the transition from different anatomical regions into one another, for example from the spinal column into the head region.

The point in the selected anatomical region that forms the origin of the whole-body coordinate system can be established automatically, in particular as a center and/or internal point of the region. Particularly within a large anatomical region, a less mobile structure (for example in the center) can be selected, for example with a relation to the shown bone structures or organs. It can also be appropriate to establish a point as the origin is different from the center, such as an inner point of the region that is again less mobile. Pathological findings (for example in the center of an anatomical region fittingly selected for monitoring) can be made that form the basis for subsequent examination images to be produced, in which case the image center naturally can be different from the center of an organ or a structure. In particular for small anatomical regions, it can be meaningful to select an eccentric origin point, for example in order to avoid the origin of the whole-body coordinate system (disadvantageous for representation purposes) from falling into the region of a possible pathological finding, whereby the risk additionally exists that anatomical variations may arise within this pathological region due to effected operations or the like. The internal point of the region in the sense of the invention can also be a known anatomical marker; such a one can thus be specified in the selected anatomical region.

The whole-body overview image and/or partial images (that, for example, were created in the framework of different examinations) can be mapped to one another, particularly by means of an iterative error correction method. Initially only rough correlations and deviations are determined, for example in order to implement a size adaptation, whereupon corrections can then be implemented step-by-step using specific image information. Such a superimposition of the whole-body overview images or partial images that were produced at various points in time enables errors to be avoided in the arrangement of the examination images in the original whole-body coordinate system, since inconsistencies as well as fundamental differences (for example with regard to the orientation) can be detected and accounted for with the mapping of the overview images or partial images to one another.

The (at least one) whole-body image and/or partial image preferably is (are) created with a medical imaging apparatus, in particular with the same examination apparatus as the examination (diagnostic) images. For example, what is known as a pre-scan can be produced for this purpose in which a complete localization of the body is created by moving a patient table on which the patient is located is moved. The overview image or partial image in this manner created not only enables a sufficiently-detailed anatomical orientation in order to establish an anatomical region, but also can be used in order to obtain fundamental examination results that are relevant for the planning of the further examination, such as, for example, the presence of distinct anatomical anomalies.

Furthermore, at least one overview image and/or partial image can be created using at least one image acquisition modality, in particular a camera and/or a laser system, and/or with the aid of a program. Such a procedure is particularly suited when an examination with diagnostic image acquisitions should not follow immediately or an examination apparatus is used with which whole-body exposures are not possible, or which would entail an unnecessarily high exposure of the patient (for example by radiation). In such a case, additional image acquisition modalities can be connected via corresponding input and output connections, in particular to the control device of a medical examination apparatus. Depending on the desired precision or detail resolution or preferred type of later representation, cameras in the optical or in the infrared range can be used as well as laser systems that scan the body. Alternatively, an overview image or partial image of a computer program can be used, for example a simple pictogram of the human body that, if applicable, is made more precise by individual specifications regarding the examination subject (such as size or weight). An overview image creation or partial image creation by means of a combination of various techniques is possible, for example an image acquisition with a camera or the like and a subsequent image processing with the aid of a program.

An image with lower resolution can be created as the overview image and/or partial image. The resolution must merely be sufficient to allow determination of an anatomical region. The generation of an overview image or partial image with resolution sufficient in this regard offers the advantage that this can be acquired more quickly than a high resolution image, while at the same time the image data quantity is limited.

In addition to the origin, at least one further point preferably is established as a marker in the whole-body overview image. Such further point serves as a marker in addition to the origin and can be automatically determined, for example using a geometric sectioning of the overview image or as an anatomically distinguished point. It is likewise possible for the doctor or technical assistant implementing the examination to determine one or more further points as markers, if applicable as a result of a prior selection of further anatomical regions. This can ensue, for example, with regard to the underlying pathological condition that is present in the respective patient.

For example, additional markers enable the use of the established whole-body coordinate system even when anatomical alterations occur in the patient that lead to the situation that an original marker or origin point can no longer be used. This can be the case, for example, when a tumor forms or when operative procedures ensue that entail anatomical changes. It is likewise possible that a patient has an accident that causes irreparable injuries, such that the origin point can no longer be determined. Given determination of additional markers, the whole-body coordinate system nevertheless still can be used as a coordinate system forming the basis of all examinations with imaging apparatuses, available for the lifespan of the patient. With increasing age, however, a matching or an adaptation is desirable.

The examination images additionally can be arranged in an examination-based coordinate system. For example, in the case of a magnetic resonance examination such an examination-based coordinate system is based on the position of the magnet and is advantageous for monitoring the positioning of the produced images with regard to this specific examination apparatus. An additional spatial reference possibility results by the use of such an examination-based coordinate system, whereby the possibilities for examination evaluation are further improved.

Magnetic resonance apparatuses and/or computed tomography apparatuses and/or x-ray apparatuses and/or positron emission apparatuses and/or ultrasound systems can be used as imaging medical examination apparatuses. The use of all imaging methods in medicine is generally conceivable, for example all corresponding nuclear medicine methods. Should the overview images also be created with the imaging medical examination apparatus, an examination apparatus is thus to be used that enables whole-body examinations. With the whole-body coordinate system according to the invention it is then possible to spatially arrange all medical image exposures in the uniform whole-body coordinate system that is defined once.

It is furthermore advantageous for information about the whole-body coordinate system is integrated into standardized image information. Such standardized image information is normally created as a "header" with regard to all image exposures and is later transferred with these exposures (i.e., the image data thereof possibly for forwarding the exposures. Here, for example, the position of the patient or the orientation during the acquisition, the acquisition time as well as duration is stored. An already-present information system can thus be used in order to store additional information with regard to the whole-body coordinate system.

Based on the whole-body overview image, possible movement of the examination subject given the generation of the examination images can be detected and/or calculations can be corrected. For this purpose, a comparison of the examination images with the overview image is implemented, and this can be implemented with less time with the aid of fit algorithms, for example an approach that is based on the nearest approximation.

Moreover, the above object is achieved in accordance with the present invention by an apparatus for acquisition and evaluation of image data of an examination subject that are generated with at least one imaging medical examination apparatus, the apparatus being designed for implementation of the method as described.

Such an apparatus normally includes a server at which the incoming image data are stored centrally. In addition, generally more than one examination apparatus will be present, for example a magnetic resonance tomography apparatus, a computed tomography apparatus and an x-ray apparatus and ultrasound apparatus. The examination apparatuses respectively possess some control devices that in turn include a computer and an image output unit that is operated by a doctor or medical assistant via a corresponding input device. The apparatuses as well as the central server are connected with one another via a network, such that with an appropriate authorization, access is possible to image data that were acquired earlier in the framework of a first examination with the same or a different examination apparatus. Should a follow-up examination now be implemented, for example with a magnetic resonance tomography apparatus, an overview image is in turn created as a pre-scan. The actual examination images are subsequently acquired. The new examination images can be arranged in multi-dimensional coordinate space with the whole-body coordinate system already determined in a preceding examination, whereupon a comparison of image information of the examination images with the new whole-body overview image is implemented.

DESCRIPTION OF THE DRAWINGS

FIG. 2 schematically illustrates an embodiment of the inventive apparatus.

FIG. 3 shows an overview image for use in the inventive method.

DESCRIPTION OF THE PREFERRED EMBODIMENTS

Figure 1:
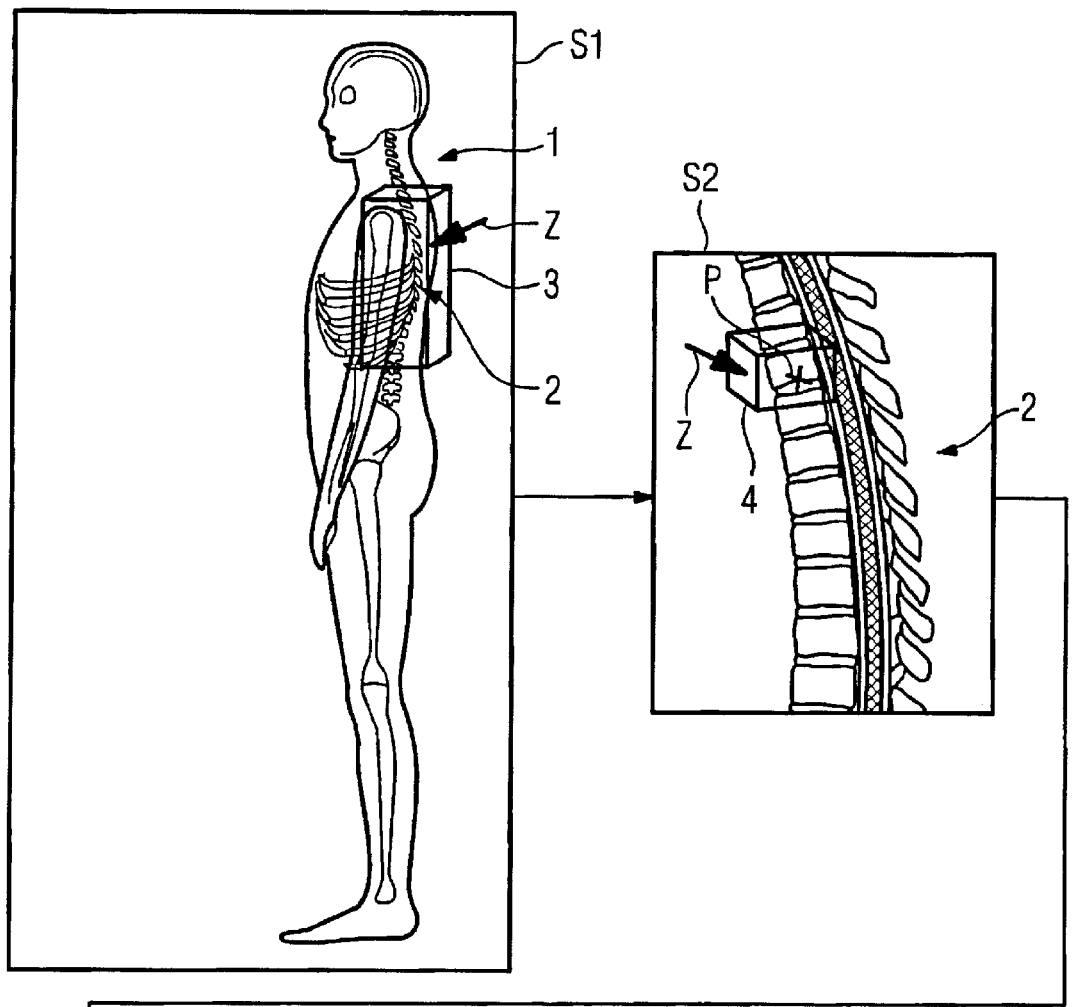
FIG. 1 is a diagram of an embodiment of the inventive method.
Figure 1:
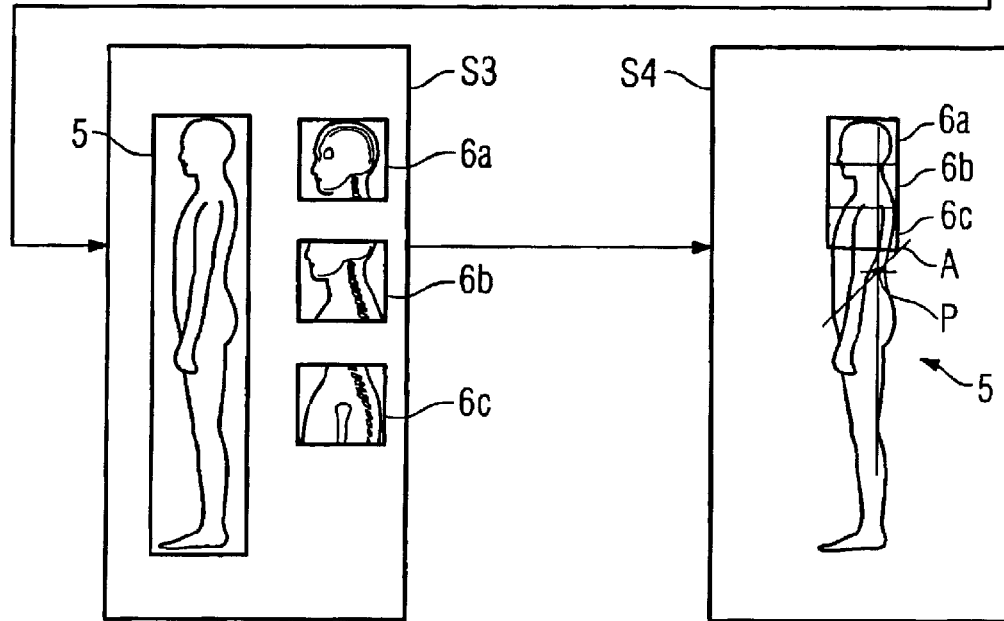

FIG. 1 shows workflow diagrams of an embodiment of the inventive method. In step S1, a whole-body overview image 1 of the examination subject has been initially created with an imaging medical examination apparatus, in which whole-body overview image 1 bone structures are indicated in order to indicate that it is an exposure obtained with a medical imaging apparatus. The overview image in this example shows a lateral view that is based on a three-dimensional data set. Alternatively, it is possible to use two-dimensional overview images that are based, for example, on exposures in a specific slice plane.

In the whole-body overview image 1, the doctor or medical assistant who operates the examination apparatus selects an anatomical region with the mouse point Z, by drawing a selection box 3 with the mouse pointer Z by means of an image processing program. In step S2, the selected anatomical region 2 (which here corresponds to a segment of the spinal column) is shown enlarged. A point forming the origin of a whole-body coordinate system with regard to the examination subject is established by drawing a further selection box 4, again by means of the mouse pointer 4. This occurs via a program that selects an anatomically-appropriate point within the selection box 4 (that here was extended over a specific vertebra). This origin point is designated with P. Starting from the origin point P, a whole-body coordinate system is determined with orthogonal axes that correspond to the typical axial directions in the anatomy relative to the body.

In step S3, a follow-up examination with a different examination apparatus is finally implemented. A whole-body overview image 5 is acquired again, which here is an overview image that was created with a camera, thus not the actual medical imaging apparatus. The camera image shows the patient again in a lateral view. The camera image is used in this case in order to keep the radiation exposure due to the medical imaging apparatus as low as possible. After the creation of the whole-body overview image 5, subsequent examination images 6a through 6c are acquired that show the head, neck and shoulder regions of the patient.

For step S4, the whole-body overview image 5 is shown again, but this time with the whole-body coordinate system with the origin point P as well as the axes A as it was established in step S2. Furthermore, the examination images 6a through 6c are shown in their spatial arrangement in the whole-body coordinate system with the origin point P. This arrangement occurred based on a comparison of at least one item of image information of the respective examination images 6a through 6c with at least one item of image information (relative to the origin point P) of the newly-created whole-body overview image 5. One or more selected points of the examination images 6a and 6c that can be inserted into the coordinate system using the position of the corresponding points in the whole-body overview image 5 (which can be associated with the whole-body coordinate system) serve as such image information. In addition to this, curve contours of anatomical structures can be taken into account. The arrangement, if applicable, can be augmented by a superimposition of both overview images, which is not shown here.

FIG. 2 shows an inventive apparatus 7 for acquisition and evaluation of image data of an examination subject to be generated with imaging medical examination apparatuses. Shown is an existing magnetic resonance apparatus 8 that has an MR scanner 9 with a basic field magnet, a gradient and RF system as well as a patient bed 10, whereby a connection to a control device 12 for the magnetic resonance apparatus 8 being established via a data connection 11. The control device 12 has a computer 12a with an image output unit 12b that can be operated via an input device 12c. Initially an overview image of a patient is acquired with the magnetic resonance apparatus 8, which overview image is subsequently displayed on the representation region D of the image output unit 12b.

Within the overview image, the operator of the control device 12 now selects an anatomical region of interest, appropriately the region at which an examination should be implemented. The selection of this anatomical region ensues from a series of predetermined regions. After the selection of the anatomical region by the operator of the control device 12, an origin point for a whole-body coordinate system to be determined is automatically established using a program stored in the computer 12a. The coordinate system is ultimately established dependent on axes that are predetermined or can be selected as needed. The actual examination exposures are subsequently finished and arranged in the whole-body coordinate system as well as in a coordinate system specific for the measurement apparatus.

The control device 12 of the magnetic resonance apparatus 8 is connected via a network N with other control devices (such as the control device 13, having a computer 13a with an image output unit 13b and a input device 13c, which belongs to an x-ray apparatus 14). The connection of the network N to further control devices is indicated by the arrow P'. A connection additionally exists to a server system 15 that is equipped (via a computer 15a with an image output unit 5b and an input device 15c) for operation by an administrator. The image exposure data as well as the overview images that serve as a reference are centrally stored in the computer 15a. Should these be viewed at a control device 12 or 13, an access to the server 15 ensues.

If the patient is now re-admitted to the hospital for a follow-up examination with the x-ray apparatus 14, a whole-body overview image of the patient (located on the patient bed 17 for this) is now acquired in turn by means of a camera 16. This overview image is initially stored in the computer 13a of the control device 13 and displayed on the image output unit 13b. The actual examination images of the examination subject are subsequently finished with the x-ray acquisition unit 18. These are subsequently arranged in the original whole-body coordinate system by a comparison with the information of the new whole-body overview image, in that characteristic values (the position of anatomical points and the like) are compared. After a post-processing (ensuing, if applicable, on the control device 13), the new whole-body overview image as well as the examination images suitable for further usage are transmitted to a computer 15a of the server system 15. A fast discovery of images without problems is inventively possible for a specific region unambiguous established by the whole-body coordinate system; only the corresponding coordinates must be specified. The quality of the examination reports is clearly improved while at the same time a simple navigation is possible in the examination planning or also in the subsequent evaluation.

FIG. 3 shows an example of an overview image 19 for use in the framework of the inventive method. Various anatomical regions 20 that here are emphasized relative to one another by rectangles are provided in the overview image 19. The overview image 10 is a two-dimensional section view. One of the anatomical regions 20 (predominantly the right leg) is selected by the operator, whereby the selection here is characterized by an emphasized rectangle 21. Within the rectangle 21, which here stands for the anatomical region of the right leg, a marker point U is established by a program as an internal point. Starting from this marker point U, the relation to a whole-body coordinate system is determined with an origin point.

In addition, further marker points M in the coordinate system established via the origin point with corresponding associated axes are specified that correspond to points in the body of the patient that can be determined well in image examinations. These additional marker points M allows the coordinate system that is established via the origin point to also be used when the original marker point U can no longer be used due to anatomical changes, for example due to an accident or an operation. After the establishment of the whole-body coordinate system as well as of the further marker points M, the actual examination exposures for the anatomical region of the right leg can be produced, whereby the whole-body coordinate system is available at any time in further examinations for unambiguous association of the examination images then produced, independent of the apparatus-specific coordinate systems as well as patient-related coordinate systems limited to a specific acquisition region.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquisition and evaluation of image data of an examination subject that are to be created with at least one medical imaging apparatus comprising the steps of:
   generating a whole body overview image of the examination subject and selecting an anatomical region in the whole-body overview image;
   electronically establishing a point in the selected anatomical region, said point forming the origin of a whole-body coordinate system relating to the examination subject, and electronically establishing an associated, subject-related coordinate system;
   in a subsequent examination with a medical imaging apparatus, re-creating a new image selected from the group consisting of a new whole-body overview image of the examination subject containing said origin, a new whole-body overview image of the examination subject containing another marker point, a partial image of the examination subject containing the origin, and a partial image of the examination subject containing another marker point, and generating examination images of the examination subject; and
   using said new image, automatically electronically spatially arranging the examination images in said whole body coordinate system by comparing at least one item of image information in each examination image with at least one item of information of the new image that is related to the whole-body coordinate system.

2. A method as claimed in claim 1 wherein the step of selecting said anatomical region in said whole-body overview image comprises manually selecting an anatomical region in said whole-body overview image.

3. A method as claimed in claim 2 comprising allowing free selection of said anatomical region by said user.

4. A method as claimed in claim 2 comprising providing said user with a plurality of predetermined anatomical regions, and restricting selection of said anatomical region by said user from among said plurality of predetermined regions.

5. A method as claimed in claim 4 comprising generating said predetermined anatomical regions from at least one basis selected from the group consisting of geometric data of the examination subject, fitting algorithms, and decision rules.

6. A method as claimed in claim 1 wherein the step of selecting said anatomical region in the whole-body overview image comprises automatically electronically selecting an anatomical region in the whole-body overview image.

7. A method as claimed in claim 1 comprising automatically electronically establishing said point forming the origin of said whole-body coordinate system in the selected anatomical region.

8. A method as claimed in claim 7 comprising selecting a center point in said selected anatomical region as said origin.

9. A method as claimed in claim 1 wherein the step of generating said new image comprises generating a new whole-body image of the examination subject and a new partial image of the examination subject, and mapping said new whole-body image and said new partial image to one another in an iterative error correction technique.

10. A method as claimed in claim 1 comprising said new image with the same medical imaging apparatus used for generating said examination images.

11. A method as claimed in claim 1 comprising generating said new image with an image acquisition unit selected from the group consisting of a camera and a laser system and an image generating computer program.

12. A method as claimed in claim 1 comprising said new image with a lower image resolution compared to an image resolution of the examination images.

13. A method as claimed in claim 1 comprising, in addition to said origin, establishing at least one further point as marker in said whole-body overview image.

14. A method as claimed in claim 1 comprising additionally arranging said examination images in an examination-based coordinate system.

15. A method as claimed in claim 1 comprising at least one of said whole-body overview image and said new image with a medical imaging apparatus selected from the group consisting of magnetic resonance imaging apparatus, computed tomography apparatuses, x-ray apparatuses, positron emission apparatuses, and ultrasound systems.

16. A method as claimed in claim 1 comprising integrating information describing said whole-body coordinate system into standardized image information.

17. A method as claimed in claim 1 comprising identifying an occurrence of movement of said examination subject between said whole-body overview image and said examination images.

18. A method as claimed in claim 17 comprising if said movement is detected, generating a corrected examination image wherein said movement is electronically computationally corrected.

19. An apparatus for acquisition and evaluation of image data of an examination subject that are to be created with at least one medical imaging apparatus comprising the steps of:
   a data acquisition device that generates a whole body overview image of the examination subject and electronically selects an anatomical region in the whole-body overview image;
   a display allowing electronic establishment of a point in the selected anatomical region, said point forming the origin of a whole-body coordinate system relating to the examination subject, and electronically establishing an associated, subject-related coordinate system;
   a medical imaging apparatus that, in a subsequent examination, re-creates a new image selected from the group consisting of a new whole-body overview image of the examination subject containing said origin, a new whole-body overview image of the examination subject containing another marker point, a partial image of the examination subject containing the origin, and a partial image of the examination subject containing another marker point, and generating examination images of the examination subject; and a computer that using said new image, automatically spatially arranges the examination images in said whole body coordinate system by comparing at least one item of image information in each examination image with at least one item of information of the new image that is related to the whole-body coordinate system.

* * * * *